US00PP22500P2

(12) United States Plant Patent
Kordes

(10) Patent No.: US PP22,500 P2
(45) Date of Patent: Feb. 21, 2012

(54) MINIATURE ROSE PLANT NAMED 'KORBURNAB'

(50) Latin Name: *Rosa hybrida*
Varietal Denomination: KORburnab

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/660,461

(22) Filed: Feb. 25, 2010

(51) Int. Cl.
*A01H 5/00* (2006.01)

(52) U.S. Cl. ..... Plt./117

(58) Field of Classification Search ..... Plt./117, Plt./124
See application file for complete search history.

(56) References Cited

U.S. PATENT DOCUMENTS

PP19,638 P2 * 1/2009 Kordes ..... Plt./117

* cited by examiner

*Primary Examiner* — June Hwu

(57) ABSTRACT

A new and distinct variety of miniature rose with long lasting, novel white flowers, and dark green and attractive foliage. It exhibits compact, uniform growth and flowering under greenhouse conditions when grown as a potted floral plant. The new variety propagates well from cuttings and by grafting. This new and distinct variety has shown to be uniform and stable in the resulting generations from asexual propagation.

1 Drawing Sheet

SUMMARY OF THE INVENTION

Genus, species and variety denomination: The botanical classification of the new rose plant is *Rosa hybrida,* 'KORburnab'.

CROSS REFERENCES AND FEDERAL R&D STATEMENT

There are no cross referenced or related applications. This variety was developed without the aid of any research grant.

BACKGROUND OF THE INVENTION

The present discovery constitutes a new and distinct variety of a miniature pot rose plant which was discovered in a cultivated area in February, 2009. The new rose variety resulted from a naturally occurring mutation of unknown causation on a basal shoot of 'KORpagbel', a patented rose from the inventor described and illustrated in U.S. Plant Pat. No. 17,183 issued on Nov. 7, 2006. The cultivated area consists of a glasshouse located at the nursery of the inventor located in Offenseth-Sparrieshoop, Germany.

The new rose plant was asexually propagated by vegetative cuttings for further evaluation. This new and distinctive miniature rose variety is named 'KORburnab'.

SUMMARY OF THE DISCOVERY

The new rose plant may be distinguished from 'KORpagbel' by the following combination of characteristics:

1. Upon opening, the petal color of 'KORburnab' is White Group 155B. The petal color of 'KORpagbel' upon opening is Red Group 49B.

2. Upon opening, the petaloid color of 'KORburnab' is White Group 155B. Upon opening, the petaloid color of 'KORpagbel' is Red Group 41C.
3. The growth of 'KORburnab' is less vigorous and is more compact than the growth of 'KORpagbel'.
4. The foliage color of 'KORburnab' is Green Group 138A and the foliage color of 'KORpagbel' is Green Group 137A.

The instant plant 'KORburnab' is significantly different from other white miniatures that are known by the inventor. Several observable differences exist between 'KORburnab' and 'KORpedia', a patented rose by the inventor that is described and illustrated in U.S. Plant Pat. No. 19,638 issued on Jan. 20, 2009:

1. The average flower diameter of 'KORburnab' is 30-40 mm when open. The average flower diameter of 'KORpedia' 60 mm.
2. The foliage of 'KORburnab' is smaller than that of 'KORpedia'. The terminal leaflet of KORpedia is 45 mm(l)×25 mm(w), while the terminal leaflet of 'KORburnab' is 25-27 mm(l)×16-18 mm(w).
3. The average flower petal size of 'KORpedia' is 30-35 mm(l)×25-35 mm(w), while the average flower petal size of 'KORburnab' is 20 mm(l)×20 (w).

The new and distinct rose plant was selected due to it its:

1. Compact and uniform growth and flowering under greenhouse conditions when grown as a potted floral plant;
2. Abundant, long lasting, and attractive white flowers on upright stems;
3. Resistance to diseases encountered in greenhouse and nursery culture; and
4. Suitability for production from softwood cuttings in floral and nursery containers;

This combination of qualities is not present in prior rose cultivars known to the inventor. These objectives have been substantially achieved and in that distinguish 'KORburnab' from all other varieties of which we are aware.

As part of the rose evaluation program, Tim-Hermann Kordes asexually propagated the mutation by rooting cuttings, and conducted evaluations and observations on the resulting plants in a controlled glasshouse environment in Offenseth-Sparrieshoop, Germany in May, 2009. The resulting rooted plants exhibited distinctive physical and biological characteristics.

These initial and other subsequent propagations conducted in controlled glasshouse environments show that the foregoing and all other characteristics of 'KORburnab' come true to form and are transmitted through succeeding generations.

BRIEF DESCRIPTION OF THE DRAWING

The accompanying drawing shows as true as is reasonably possible to obtain in color photographs of this type, the typical characteristics of the buds, flowers, leaves, and stems of 'KORburnab'. Specifically illustrated is: a flower bud, partially opened bloom, open bloom, detached sepals, receptacle, peduncle, juvenile foliage, stem exhibiting thorns, and leaves.

DETAILED BOTANICAL DESCRIPTION

The following is a description of 'KORburnab', as observed in its growth in November, 2009 in a glasshouse at Offenseth-Sparrieshoop, Germany on plants of five months of age. Color references are made using The Royal Horticultural Society (London, England) Colour Chart, 2001 except where common terms of color are used.

For a comparison, several physical characteristics of the rose variety 'KORpagbel', a rose variety from the same inventor described and illustrated in U.S. Plant Pat. No. 17,183 and issued on Nov. 7, 2006 are compared to 'KORburnab' in Chart 1.

CHART 1

| Trait | 'KORburnab' | 'KORpagbel' |
|---|---|---|
| Petal Color | White Group 155B | Red Group 49B |
| Petaloid Color | Green-Yellow Group 1C | Red Group 41C |
| Sepal Color | Green-Yellow Group 144B | Green Group 137A |
| Mature Foliage Color | Green Group 138A | Green Group 137B |

Parentage: Spontaneous mutation of 'KORpagbel' (U.S. Plant Pat. No. 17,183).

Classification:

*Botanical classification.*—*Rosa hybrida*, 'KORburnab'.

*Commercial classification.*—Miniature rose.

FLOWER AND FLOWER BUD

Blooming habit: Recurrent.

Flower bud:

*Size.*—Upon opening, 15-20 mm in length from base of receptacle to end of bud and 10-12 mm in diameter at its widest point.

*Bud form.*—Long. Pointed ovoid.

*Bud color.*—As sepals first unfold, bud color is White Group 155A. When ¼ open, the upper surface of petals is White Group 155A, and the lower surface is White Group 155A.

*Sepals.*—Size: Average 18-20 mm long×5-6 mm wide. Shape: Sepals generally subulate. Sepal apex is generally cirrose. Strong foliaceous appendages on three of the five sepals. Base is flat at union with receptacle. Quantity: Five. Margins: With stipitate glands. Surface texture: Inner side: Covered in fine hairs. Outer surface: Smooth. Stipitate glands are present. Color: Upper surface is Yellow-Green Group 144B. Lower surface is Yellow-Green Group 144A.

Receptacle: Surface: Smooth. Color: Yellow-Green Group 144A. Shape: Funnel. Size: 5 mm (h)×5 mm (w).

Peduncle:

*Surface.*—With stipitate glands.

*Length.*—12-15 mm average length.

*Diameter.*—1-1.5 mm average diameter.

*Color.*—Yellow-Green Group 144B.

*Strength.*—Somewhat strong.

*Borne.*—Most commonly singly, with 1-3 blooms per stem.

Flower bloom:

*Fragrance.*—Light.

*Duration.*—Long lasting. A blooming plant with flowers has a commercial shelf life of 10 to 12 days. The blooms have duration on the plant of approximately 10 to 12 days. As a cut flower, 6 to 8 days.

*Size.*—Average for a 10 cm pot rose. Average flower diameter is 30-40 mm when open. Average flower depth is 25 mm.

*Form.*—Shape of flower when viewed from the side: Upon opening, upper part: Flat. Upon opening, lower part: Flattened convex. Open flower, upper part: Flat. Open flower, lower part: Flattened convex.

Color:

*Upon opening, petals.*—Outermost petals: Outer Side: White Group 155A. Inner Side: White Group 155A. Innermost petals: Outer Side: Green-Yellow Group 1D. Inner Side: Green-Yellow Group 1D.

*Upon opening, basal petal spots.*—Basal petal spot, outermost petals: Outer Side: Green-Yellow Group 1C. Inner Side: Yellow Group 2B. Basal petal spot, innermost petals: Outer Side: Yellow Group 2B. Inner Side: Yellow Group 2B.

*After opening, petals.*—Outermost petals: Outer Side: White Group 155B. Inner Side: White Group 155B. Innermost petals: Outer Side: Green-Yellow Group 1D. Inner Side: Green-Yellow Group 1D.

*After opening, basal petal spots.*—Basal petal spot, outermost petals: No distinctive coloration at petal base observed. Basal petal spot, innermost petals: Outer Side: Yellow Group 2B. Inner Side: Yellow Group 2C. Variegations: No distinctive coloration observed.

General tonality: On open flower, tonality is White Group 155A. No change in the general tonality at the end of the $7^{th}$ day. Afterwards, general tonality is White Group 155B.

Petals:

*Petal count.*—Approximately 24-28 petals under normal conditions.

*Petal reflex.*—Petals reflex slightly.

*Petal edge.*—With point in center of margin.

*Petal shape.*—Round. Apex shape is round. Shape of base is acute.

*Petal size.*—20 mm long×20 mm wide.

*Thickness.*—Average.

*Petal arrangement.*—Not formal.

*Petaloids.*—Present.

*Petaloid count.*—Average of 4-6 per flower.

*Petaloid edge.*—With point in center of margin.

*Petaloid texture.*—Smooth.

*Petaloid shape.*—Apex: rounded. Base: pointed.

*Petaloid size.*—Petaloids are 5-6 mm long and 3-4 mm wide.

*Petaloid color.*—Color of inner side is Green-Yellow Group 1C. Color of outer side is Green-Yellow Group 1C.

Reproductive organs:

*Pistils.*—Approximately 30-40 present. Stigmas: Location: Slightly inferior in position to anthers. Color: Greyed-Yellow Group 160D. Styles: Length: 2-3 mm long. Color: Greyed-Yellow Group 160D.

*Stamens.*—Approximately 40-50 on average and regularly arranged. Anthers: Size: 2 mm long. Color: Yellow-Orange Group 16B & 16C. Pollen: Absent. Filaments: Color: Yellow Group 9A. Length: 5-6 mm.

THE PLANT

*Plant growth.*—Moderately vigorous. Upright to bushy habit. When grown as a 10 cm pot plant, the average height of the plant is 18-20 cm and the average width is 16-18 cm.

*Stems.*—Stem color: Young wood: Yellow-Green Group 144A. Older wood: Green Group 138B. Stem surface: Young wood: Smooth. Older wood: Rough.

*Prickles.*—Present. Incidence: 8-10 per 10 cm of stem. Size: Average length: 5 mm. Color: Immature prickles: Yellow-Green Group 145C. Mature prickles: Greyed-Orange Group 165C. Senescing to Greyed-Orange Group 165A. Intonations of Greyed-Red Group 182B. Shape: Linear. Anthocyanin: Greyed-Red Group 182B.

*Leaves and leaflets.*—Normally 3-5 leaflets on normal leaves in middle of the stem. Venation pattern: Pyramidal net pattern. Leaf size: 70-80 mm (l)×135-140 mm (w). Quantity: Average. Texture: Upper side of leaflet: Semi glossy. Smooth. Under side of leaflet: Matte. Rough. Color, mature foliage: Upper Leaf Surface: Green Group 138A. Lower Leaf Surface: Green Group 138B. Color, juvenile foliage: Upper Leaf Surface: Yellow-Green Group 144A. Lower Leaf Surface: Yellow-Green Group 146D. Anthocyanin intonation: Present. Location: Intonations present on leaf margins. Color: Greyed-Red Group 182A.

*Stipules.*—Size: 8-11 mm long. 7-8 mm between the tips of the stipule. Main body of stipule 3-4 mm in width. Shape: Apex: Apiculate. Base: Fused to the petiole. Stipule color: Yellow-Green Group 144A. Anthocyanin: Greyed-Red Group 182B. Presence of stipitate glands: Present on margins. Margins: With stipitate glands.

*Petiole.*—Length: 8 mm -12 mm. Diameter: 1 mm. Petiole color: Yellow-Green Group 144A. Color of anthocyanin present on juvenile tissue: Greyed-Purple Group 184B. Underneath: A few small prickles underneath. Stipitate glands: Limited numbers of stipitate glands on margins.

*Petiole rachis.*—Length: 8-10 mm. Diameter: 1 mm. Color: Yellow-Green Group 144A. Anthocyanin present on juvenile tissue. Anthocyanin color: Greyed-Purple Group 184B. Margins: With stipitate glands. Prickles: Lacking. Stipitate glands: Limited numbers of stipitate glands on margins.

*Leaflets.*—Size: Average size of the terminal leaflet is 25-27 mm (1)×16-18 mm (w). Shape: Elliptic. Base: Rounded. Apex: Acute. Surface: Upper side: Semi-glossy. Lower side: Semi-glossy to matte. Margins: Finely serrated. Texture: Thin.

Hips/seed formation: None observed. The plant has not been grown to the stage of hip and seed development due to its use as a flowering potted plant.

Winter hardiness: Due to the variety's principal use in greenhouses, winter hardiness has not been evaluated.

Disease resistance: Above average resistance to Powdery mildew (*Sphaerotheca pannosa*) and *Botrytis* (*Botrytis cinerea*) diseases under normal greenhouse growing conditions in Offenseth-Sparrieshoop, Germany.

I claim:

1. A new and distinct miniature rose plant of the variety substantially as illustrated and described herein.

* * * * *

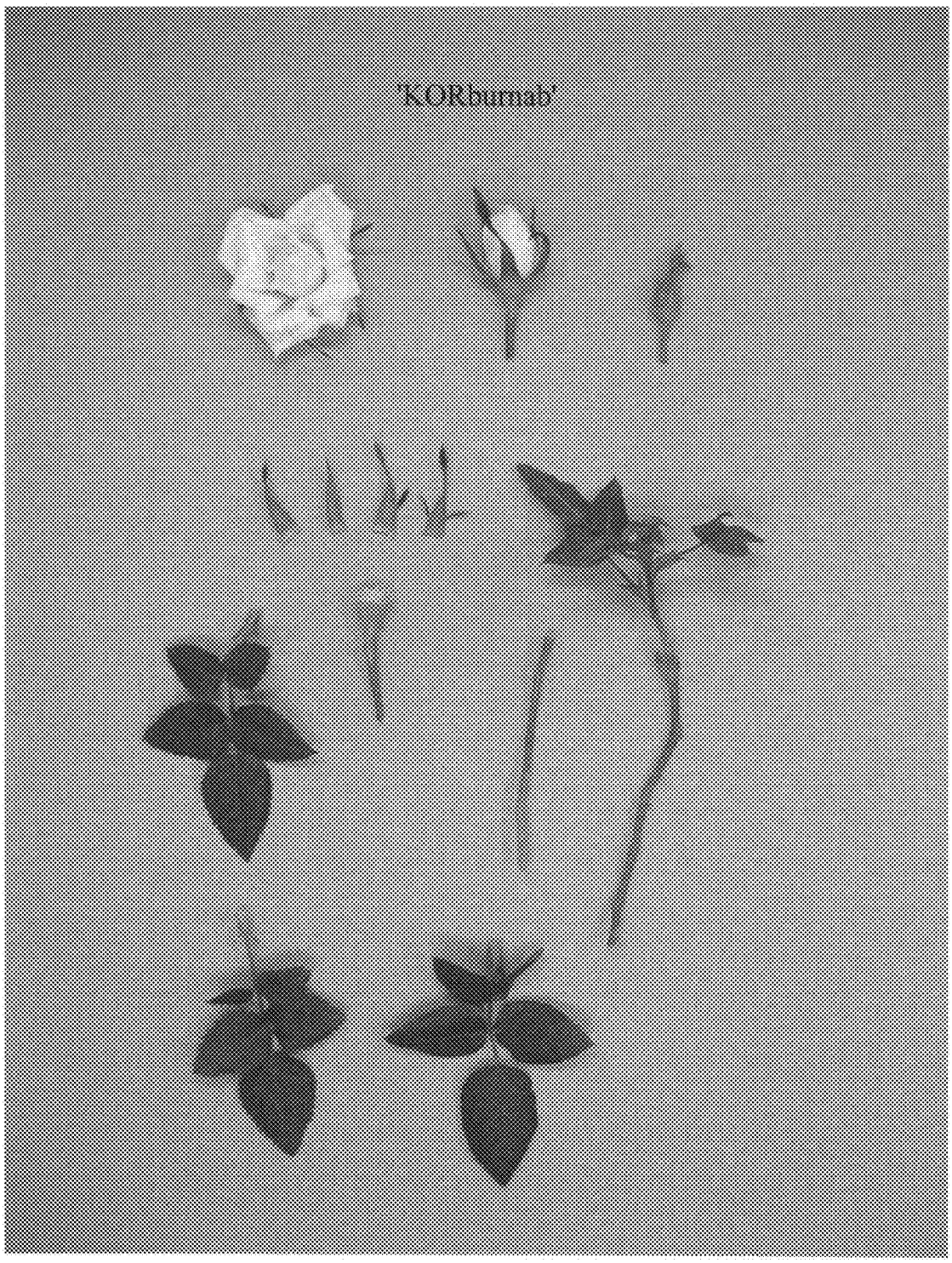
'KORburnab'